US009144544B1

(12) United States Patent
Alsalhi et al.

(10) Patent No.: US 9,144,544 B1
(45) Date of Patent: Sep. 29, 2015

(54) **SYNTHESIS OF SILVER NANOPARTICLES FROM *PIMPINELLA ANISUM* SEEDS**

(71) Applicant: KING SAUD UNIVERSITY, Riyadh (SA)

(72) Inventors: Mohamad Saleh Alsalhi, Riyadh (SA); Akram Ahmed Alfuraydi, Riyadh (SA); Sandhanasamy Devanesan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/619,022

(22) Filed: Feb. 10, 2015

(51) Int. Cl.
*A61K 9/14* (2006.01)
*A61K 33/38* (2006.01)
*A61K 36/23* (2006.01)

(52) U.S. Cl.
CPC ............. *A61K 9/148* (2013.01); *A61K 33/38* (2013.01); *A61K 36/23* (2013.01); *Y10S 977/773* (2013.01)

(58) Field of Classification Search
None
See application file for complete search history.

(56) References Cited

U.S. PATENT DOCUMENTS

| 6,037,102 | A * | 3/2000 | Loerzer et al. | 430/306 |
| 6,395,286 | B1 * | 5/2002 | Pillai et al. | 424/401 |
| 8,057,682 | B2 | 11/2011 | Hoag et al. | |
| 2011/0110723 | A1 * | 5/2011 | Varma et al. | 405/128.75 |

FOREIGN PATENT DOCUMENTS

WO    WO 2005/095031 A1    10/2005

OTHER PUBLICATIONS

A Al Maofari, S El Hajjiji, A Debbab, S Zaydoun, B Ouaki, R Charof, Z Mennane, A Hakiki, M Mosaddak. "Chemical Composition and Antibacterial Properties of Essential Oils of *Pimpinella anisum* L. Growing in Morocco and Yemen." Scientific Study & Research, ISSN 1582-540X, vol. 14(1), 2013, pp. 11-16.*
S Kadan, M Rayan, A Rayan. "Anticancer Activity of Anise (*Pimpinella anisum* L.) Seed Extract." The Open Nutraceuticals Journal, vol. 6, 2013, pp. 1-5.*
Chemical Abstracts. STN Registry Data for Trans-Anethole (CAS 4180-23-8). Entered STN Nov. 16, 1984, 5 printed pages.*
Awwad et al., "Green synthesis of silver nanoparticles using carob leaf extract and its antibacterial activity," International Journal of Industrial Chemistry, 2013, vol. 4, issue 29, pp. 1-6.
Bar et al., "Green Synthesis of Silver Nanoparticles Using Seed Extract of *Jatropha curcas*," Colloids and Surfaces A: Physicochemical and Engineering Aspects, 2009, vol. 348, pp. 212-216.
Irvani et al., "Green Synthesis of Silver Nanoparticles Using *Pinus eldarica* Bark Extract," BioMed Research International, vol. 2013, pp. 1-5.
Khadri et al., "Green Synthesis of Silver Nanoparticles with High Fungicidal Activity from Olive Seed Extract," Advances in Nanoparticles, 2013, vol. 2, pp. 241-246.

* cited by examiner

*Primary Examiner* — Isaac Shomer
(74) *Attorney, Agent, or Firm* — Richard C Litman

(57) ABSTRACT

The synthesis of silver nanoparticles from *Pimpinella anisum* L seeds includes providing a silver nitrate ($AgNO_3$) solution, providing an extract of *Pimpinella anisum* L. plant seeds, and combining the silver nitrate solution with the extract of the *Pimpinella anisum* L. plant seeds to produce silver nanoparticles. The synthesis of silver nanoparticles from *Pimpinella anisum* L. seeds does not require toxic chemical solvents.

8 Claims, 5 Drawing Sheets

SYNTHESIS OF SILVER NANOPARTICLES FROM *PIMPINELLA ANISUM* SEEDS

BACKGROUND OF THE INVENTION

1. Field of the Invention

The present invention relates to the synthesis of silver nanoparticles, and particularly to the synthesis of silver nanoparticles from *Pimpinella anisum* using an extract of the plant seed.

2. Description of the Related Art

Because of their unique properties, noble metal nanoparticles have many practical applications in the field of medicine, biology, material science, physics and chemistry. Among the noble metal nanoparticles, silver metal nanoparticles in particular have received special focus for demonstrating good electrical conductivity, chemical stability, catalytic activity, and antibacterial activity. Conventional physicochemical methods for synthesis of silver nanoparticles, however, often require the use of toxic solvents, high energy consumption, and generation of by-products. As such, there is an urgent need to develop environment-friendly methods for synthesizing silver nanoparticles (Ag NPs).

Environmentally benign synthesis, or green synthesis, of nanoparticles can provide an eco-friendly, cost effective approach to synthesis of silver nanoparticles. Green synthesis of silver nanoparticles can facilitate large scale synthesis of silver nanoparticles and help promote research on and development of silver nanoparticles.

Due to their high anti-microbial activity, silver nanoparticles have been used in a variety of applications, including food, medicine, clothing, sunscreens, and cosmetics.

Thus, synthesis of silver nanoparticles from *Pimpinella anisum* seeds solving the aforementioned problems is desired.

SUMMARY OF THE INVENTION

The synthesis of silver nanoparticles from *Pimpinella anisum* L seeds includes providing a silver nitrate ($AgNO_3$) solution, providing an aqueous extract of *Pimpinella anisum* L. plant seeds, and combining the silver nitrate solution with the extract of the *Pimpinella anisum* L. plant seeds to produce silver nanoparticles. The synthesis of silver nanoparticles from *Pimpinella anisum* L. seeds does not require toxic chemical solvents.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
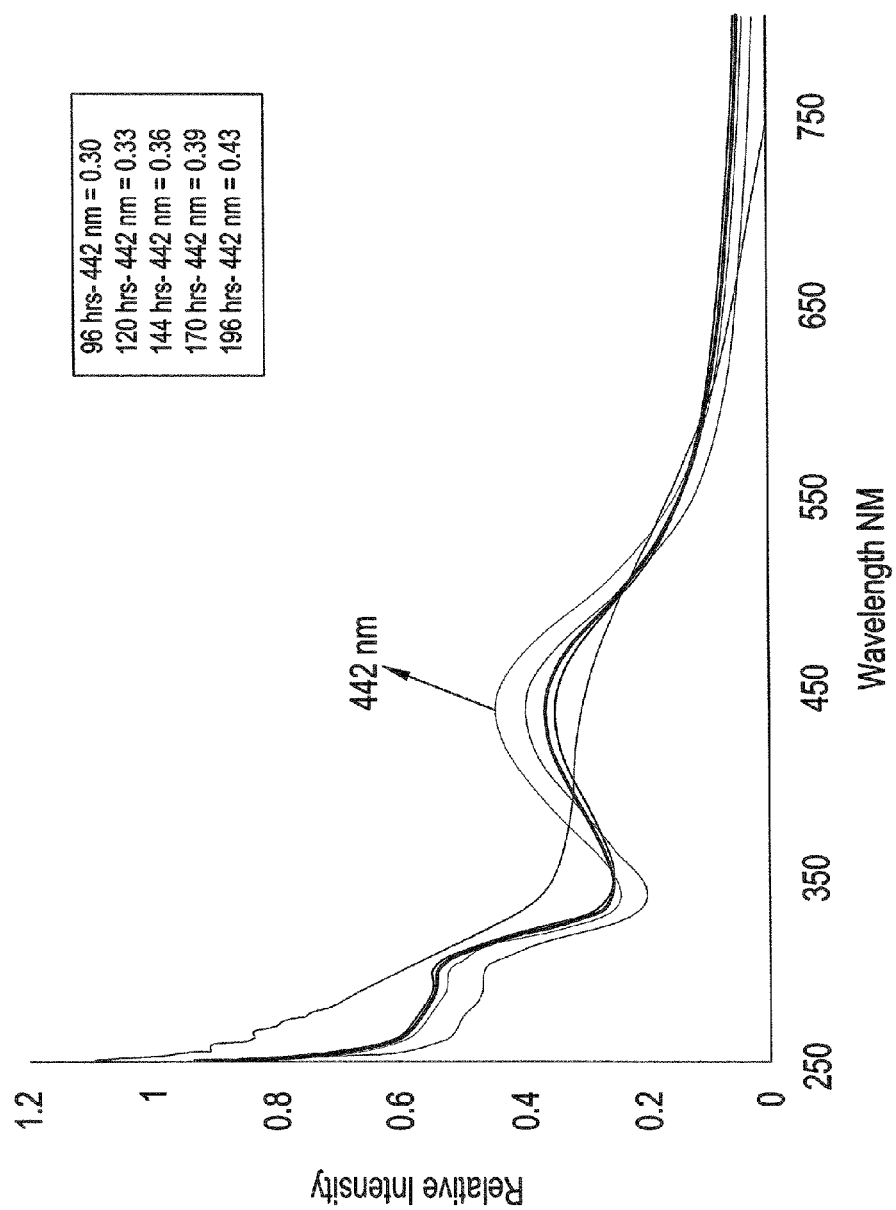
FIG. 1 is the UV spectra recorded at different time intervals of the reaction of $AgNO_3$ solution with *Pimpinella anisum* L. seed extract.

The method for synthesis of silver nanoparticles from *Pimpinella anisum* L. plant seeds can include providing a silver nitrate ($AgNO_3$) solution, providing an aqueous extract of *Pimpinella anisum* L. plant seeds, and combining the silver nitrate solution with the extract of the *Pimpinella anisum* L. plant seeds to produce silver nanoparticles.

An extract of the *Pimpinella anisum* L. plant seeds are prepared by washing the plant seeds with water, e.g., double distilled water ($D.H_2O$), to remove surface contaminations, drying the washed seeds, and then grinding the seeds to a fine powder. The washed seeds are dried at room temperature, e.g., a temperature ranging from about 15° C. to about 25° C. At room temperature, the dried seeds can require up to two days to dry. The powder is combined with or added to water, e.g., (250 ml of $D.H_2O$), and allowed to soak in the water for up to 24 hours at room temperature. The soaked mixture is filtered to provide a colorless, aqueous seed extract. The colorless seed extract is mixed with a silver nitrate solution (e.g., a 3 mM silver nitrate solution) and then left undisturbed at room temperature for approximately 96 hours or until the mixture transforms from colorless to a brown or dark color. The color transformation to a brown or dark color indicates the formation of silver nanoparticles. The particles is then purified, e.g., by centrifugation, to remove excess silver ions.

The present inventors have discovered that silver nanoparticles (SNPs) can be synthesized from the seeds of *Pimpinella anisum* L. using the methods described herein. Combining the silver nitrate solution with the plant seed extract of *Pimpinella anisum* L. under the conditions described herein reduces silver ions in the solution to thereby produce silver nanoparticles (SNPs). The synthesis of silver nanoparticles from *Pimpinella anisum* L. plant seeds is not energy intensive and does not require toxic chemical solvents. The synthesis of silver nanoparticles from *Pimpinella anisum* L. plant seeds can be a single-pot process. Accordingly, the method can provide a green approach for synthesis of nanoparticles.

The present inventors have further discovered, surprisingly, that the present method can be used to synthesize very small SNPs, e.g., about 3 nm to about 16 nm. The SNPs synthesized according to the present methods were characterized using various techniques, including transmission electron microscopy (TEM), energy-dispersive X-ray spectroscopy (EDX), Fourier transform infrared spectroscopy (FTIR), X-ray diffraction (XRD), and absorbance (UV) spectroscopy. As discussed below in detail, the results confirmed synthesis of SNPs, which where spherical and small in size.

Characterization by ultraviolet spectroscopy at 440 nm and color change revealed the formation of SNPs. While irregular-shaped particles were observed using scanning electron microscopy (SEM), transmission electron microscopy (TEM) revealed spherical shapes that ranged in size from around 3.2 nm to around 16 nm, with an average particle size of around 8.3 nm. It was found that even a minimal quantity of plant seed extract can be used to react with $AgNO_3$ and produce SNPs. The present method can be used to generate bulk quantities of SNPs. Accordingly, the present method provides a simple, cost-effective, and eco-friendly method to synthesize silver nanoparticles.

The SNPs synthesized according to the present methods can be characterized as having a high degree of dispersibility. In other words, the SNPs can be much easier to handle because they are less susceptible to aggregation than are silver nanoparticles prepared using other methods. The SNPs synthesized according to the present methods can be used in a variety of applications, including medical applications. For example, the SNPs can be incorporated into medicinal materials to provide various health benefits.

*Pimpinella anisum* L., or anise, is an annual herb and a grassy plant with white flowers and small, green or yellow seeds. *Pimpinella anisum* L., in the family Apiaceae, typically grows in the Mediterranean region, India, and other regions in the world with warm climate. *Pimpinella anisum* L. is primarily grown for its fruits (seeds), which are frequently used for flavoring as well as medicinal purposes. For example, the essential oil from *Pimpinella anisum* L. seeds has been used as a spice in foods, as a remedy in traditional medicine, and as fragrance in the perfume industry. It is believed that *Pimpinella anisum* L. seeds have antimicrobial, antifungal, antiviral, antioxidant, muscle relaxant, analgesic and anticonvulsant activity. It has further been found that *Pimpinella anisum* L. seeds can reduce lipid peroxidation in diabetic patients, as well as affecting the hypoglycemic and hypolipidemic condition.

The following examples are provided by way of illustration.

Example 1

Synthesis of Silver Nanoparticles (SNPs)

Fresh, healthy *Pimpinella anisum* L. seeds were collected from Madinah region (Saudi Arabia) and washed 10 times repeatedly with double distilled ($D.H_2O$) water to remove surface contaminant. The washed seeds were dried for 2 days at room temperature, then ground into a fine powder without any constraint. Then, 10 grams of plant powder was added to 250 ml of $D.H_2O$ and allowed to soak up to 24 hours. The soaked mixture was filtered using Whatman No. 1 filter paper. About 2.5 ml of the seed extract was combined with 250 ml of a silver nitrate ($AgNO_3$) solution (3 mM). The reaction mixture was left undisturbed for approximately 96 hours, until the colorless solution changed into a brown color (FIG. 1). All of the steps were carried out at room temperature. The particles were purified by centrifugation to remove excess silver ions. Then, the silver colloids were washed at least three times with double-distilled water. For further characterization and application purposes, the sample was stored in screw capped vials under aseptic condition.

Example 2

Characterization of SNPs by UV Spectroscopy

Ultraviolet (UV) absorption spectroscopy was used to quantify the synthesis reaction of SNPs when the plant seed extract of *Pimpinella anisum* L. was combined with the silver nitrate solution in accordance with the method described in Example 1. FIG. 1 shows the UV spectra recorded at different reaction time intervals (96 hours, 120 hours, 144 hours, 170 hours, and 196 hours) after starting the reaction. The spectra show that the concentration of intensity ratio was 0.30, 0.33, 0.36, 0.39, and 0.43 for the respective time intervals. Accordingly, the intensity ratio increased with time until about 196 hours. After 196 hours, there was no significant level of intensity ratio increase. This reaction was stable and no aggregation of particles was reported.

Example 3

Characterization of SNPs by FTIR

Figure 2:
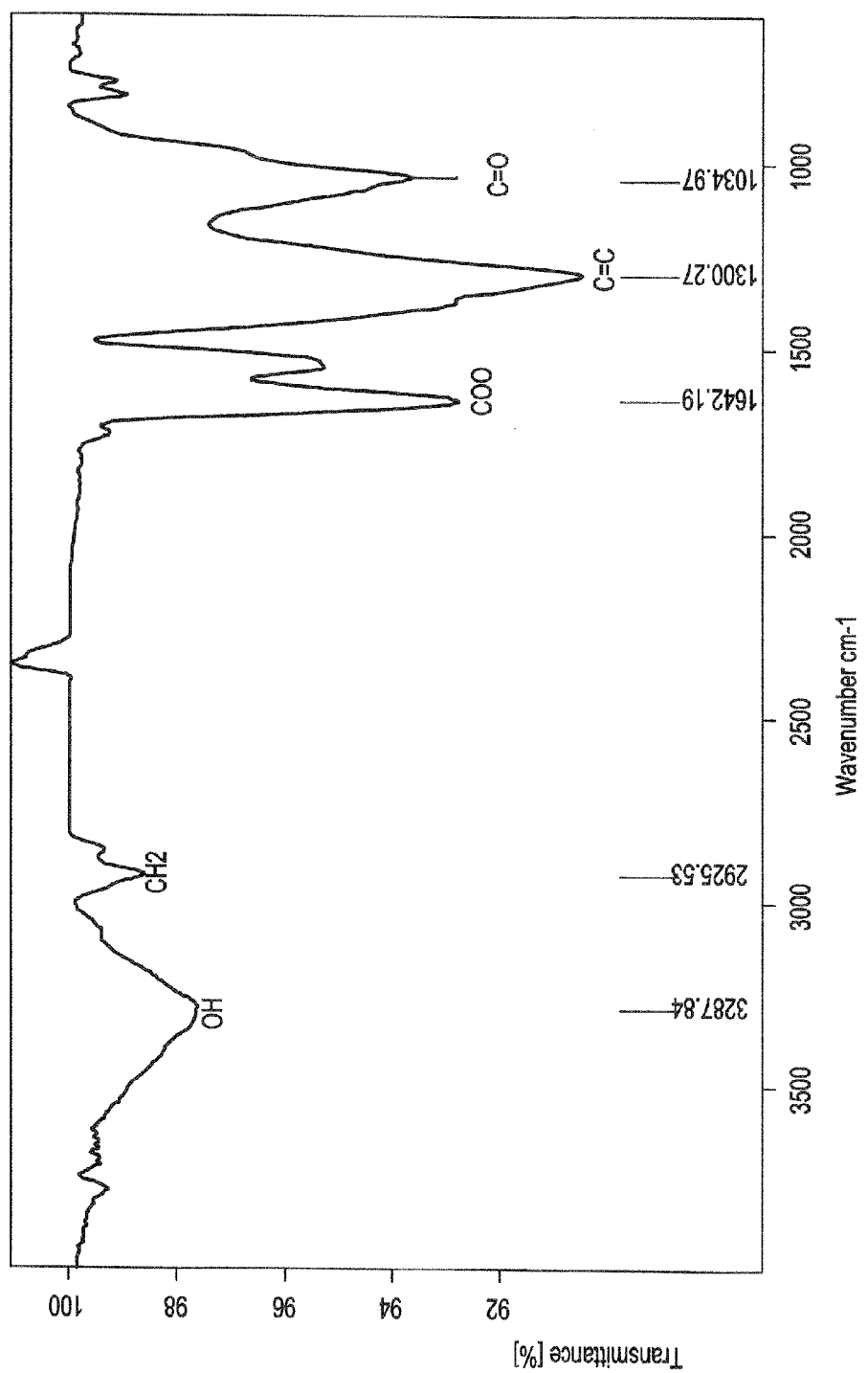
FIG. 2 is the FTIR spectrum recorded of the product of reacting $AgNO_3$ solution with *Pimpinella anisum* L. seed extract.

Fourier transform infrared (FTIR) spectroscopy was used for further quantitative analysis of the reaction described in Example 1 and to identify chemical bonds. The FTIR spectrum of the product of the reaction of silver nitrate solution with the *Pimpinella anisum* L. seed extract is shown in FIG. 2. The spectrum shows five bonds at 3287, 2925, 1642, 1300, and 1034 nm, respectively, due to OH, CH, COO, C=C, and C=O. In addition, the spectrum showed the presence of active biomolecules in the plant seed extract of *Pimpinella anisum* L. This confirms the synthesis of silver nanoparticles.

Example 4

Characterization of SNPs by XRD Crystallography

Figure 3:
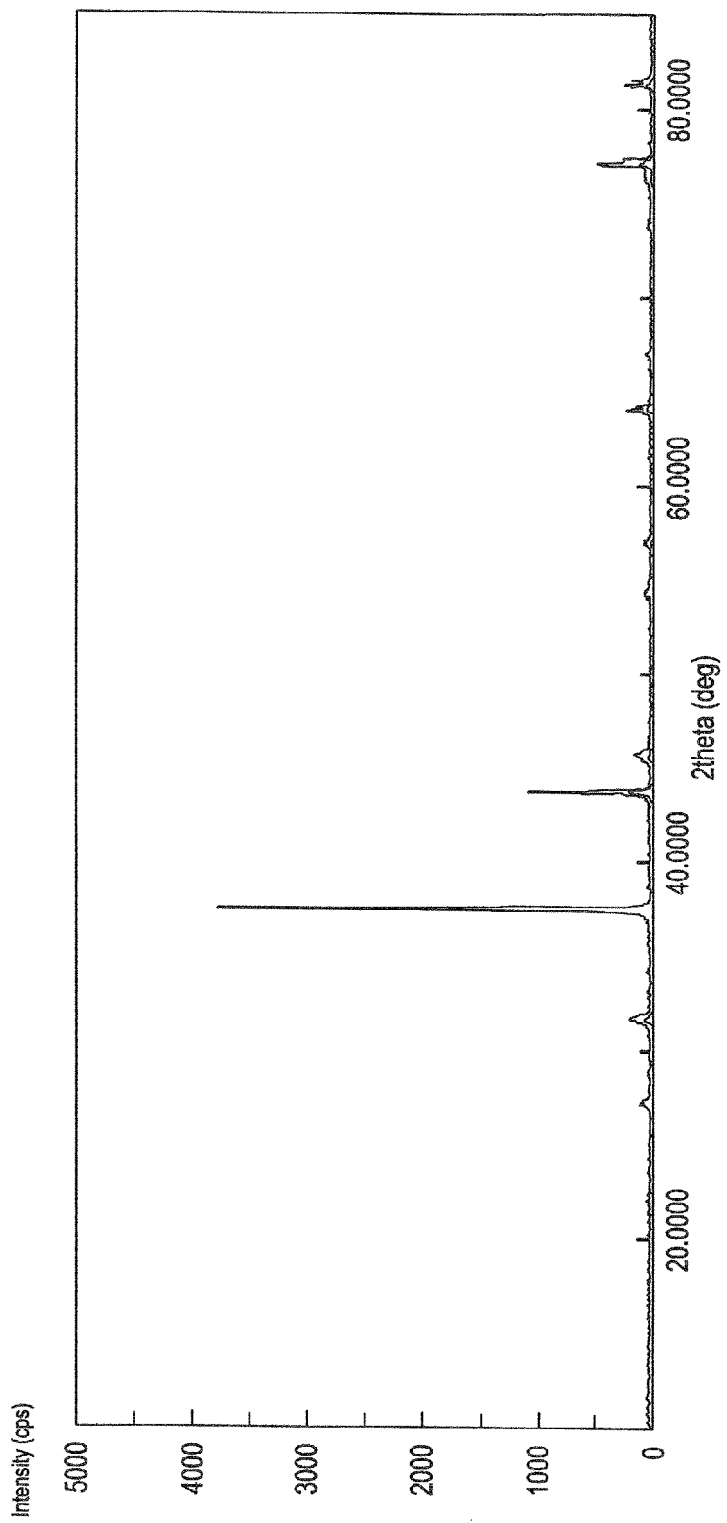
FIG. 3 is a crystal X-ray diffraction (XRD) measurement of the product of reacting $AgNO_3$ solution with *Pimpinella anisum* L. seed extract.

The X-ray diffraction analysis pattern (XRD) of the product of the reaction of silver nitrate solution with the *Pimpinella anisum* L. seed extract, shown in FIG. 3, confirms the crystalline nature of the SNPs synthesized according to the method described in Example 1. The XRD analysis pattern indicates four main characteristic peaks at 2 theta values of 38°, 44°, 65° and 78°, respectively.

Example 5

Characterization of SNPs by TEM Microscopy

Figure 4:
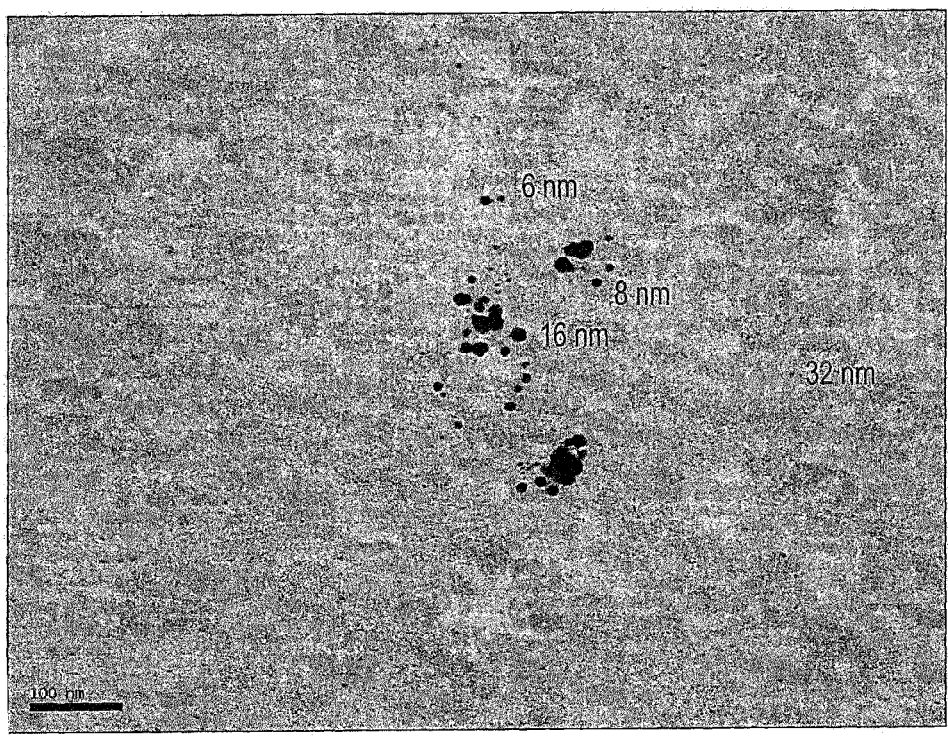
FIG. 4 shows a transmission electron microscopy (TEM) micrograph of silver nanoparticles synthesized by synthesis of silver nanoparticles from *Pimpinella anisum* L seeds according to the present invention.

Transmission electron microscopy (TEM) images of the product of the reaction of silver nitrate solution with the *Pimpinella anisum* L. seed extract were obtained to further confirm synthesis of the silver nanoparticles, which were exhibited as individual silver particles and also a number of aggregates. A TEM image from carbon coated samples of the aqueous solution immersed with *Pimpinella anisum* L. is shown in FIG. 4. The morphology of the nanoparticles observed was variable. Smooth surface of independent dispersed particles were observed. Spherical shapes ranging from around 3.2 nm to around 16 nm in size were observed. The average size of the spherical shapes was around 8.3 nm.

Example 6

Characterization of SNPs by Energy Dispersive X Ray Diffraction (EDX)

Figure 5:
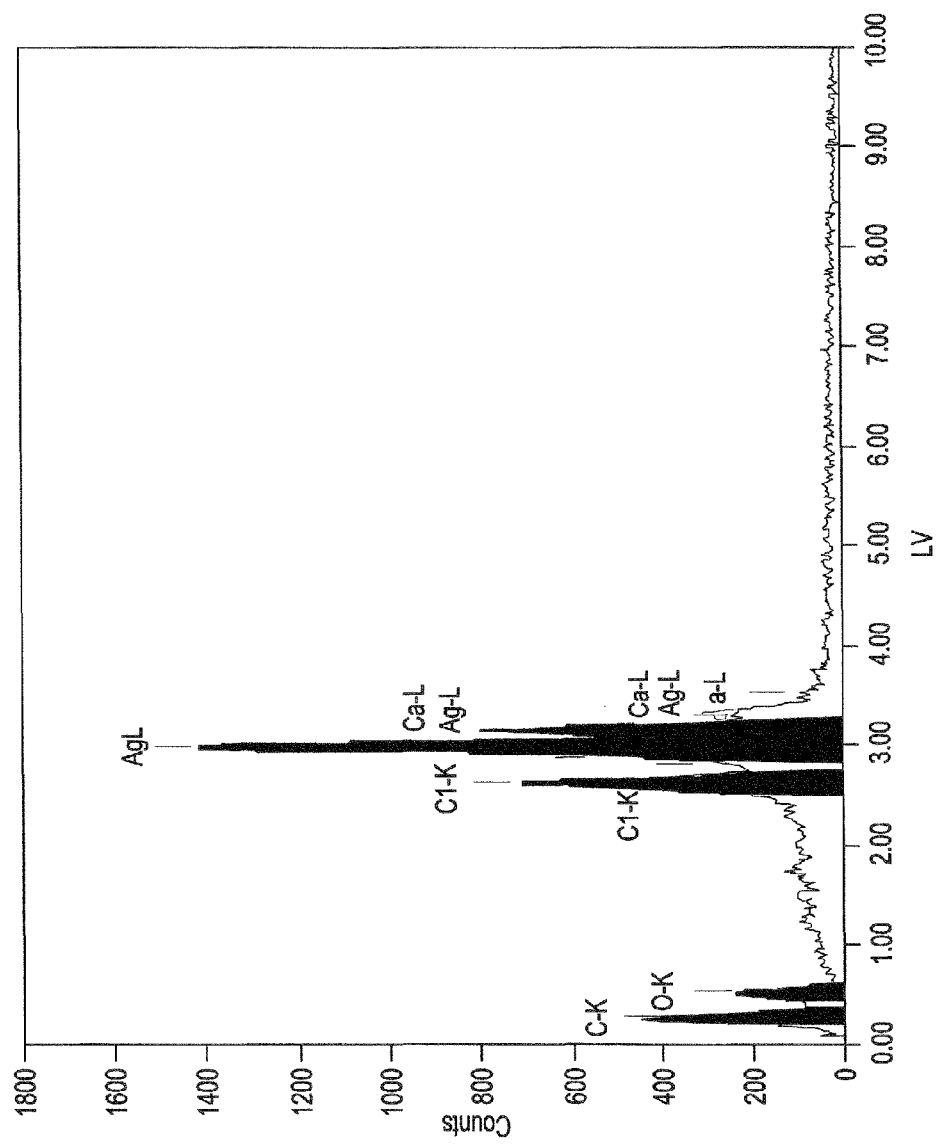
FIG. 5 is the energy dispersive X-spectroscopy (EDX) spectrum of the product of reacting $AgNO_3$ solution with *Pimpinella anisum* L. seed extract.

Energy dispersive X ray diffraction (EDX) analysis of the product of the reaction of silver nitrate solution with the *Pimpinella anisum* L. seed extract recorded the elemental composition profile of the synthesized SNPs. As shown in FIG. 5, the intense signal at 3 keV confirmed that Ag was the major element of these NPs. The other intense signals (carbon, oxygen, potassium and hydrogen) indicated the presence of plant extract, which corresponds to the biomolecules overlapping the SNPs.

It is to be understood that the present invention is not limited to the embodiments described above, but encompasses any and all embodiments within the scope of the following claims.

We claim:

1. A method for synthesis of silver nanoparticles from *Pimpinella anisum* L. seeds, comprising the steps of:
   providing a silver nitrate ($AgNO_3$) solution;
   providing a colorless, aqueous extract of *Pimpinella anisum* L. plant seeds; and
   combining the silver nitrate ($AgNO_3$) solution with the extract of *Pimpinella anisum* L. plant seeds to obtain silver nanoparticles (SNPs).

2. The method for synthesis of silver nanoparticles according to claim 1, wherein the step of providing the colorless, aqueous extract of *Pimpinella anisum* L. plant seeds comprises:
   washing *Pimpinella anisum* L. plant seeds with water to obtain washed seeds;
   drying the washed seeds at room temperature to obtain dried seeds;
   grinding the dried seeds to a fine powder;
   soaking the powder in water to obtain a soaked mixture; and
   filtering the soaked mixture to obtain a colorless, aqueous seed extract.

3. The method for synthesis of silver nanoparticles according to claim 1, wherein the volume ratio (v/v) of colorless, aqueous extract to $AgNO_3$ is about 1:100.

4. The method for synthesis of silver nanoparticles according to claim 3, wherein the step of combining the silver nitrate ($AgNO_3$) solution with the colorless, aqueous extract of *Pimpinella anisum* L. plant seeds further comprises maintaining the mixture produced by combining the colorless, aqueous extract of *Pimpinella anisum* L. plant seeds with the silver nitrate ($AgNO_3$) solution at room temperature until a color change is detected in the mixture.

5. The method for synthesis of silver nanoparticles according to claim 4, wherein the mixture produced by combining the colorless, aqueous extract of *Pimpinella anisum* L. plant seeds and the silver nitrate ($AgNO_3$) solution is maintained at room temperature for about 96 hours.

6. The method for synthesis of silver nanoparticles according to claim 1, wherein the silver nanoparticles have a size between 3.2 nm and 16 nm.

7. The method for synthesis of silver nanoparticles according to claim 1, wherein the silver nanoparticles have an average size of about 8 nm.

8. The method for synthesis of silver nanoparticles according to claim 1, wherein the silver nitrate ($AgNO_3$) solution has a concentration of about 3 mM.

* * * * *